US012121503B2

(12) United States Patent
Babu et al.

(10) Patent No.: US 12,121,503 B2
(45) Date of Patent: *Oct. 22, 2024

(54) ANTIVIRAL TREATMENTS

(71) Applicant: BIOCRYST PHARMACEUTICALS, INC., Durham, NC (US)

(72) Inventors: Yarlagadda S Babu, Birmingham, AL (US); Pooran Chand, Birmingham, AL (US); Shanta Bantia, Birmingham, AL (US); Shane Arnold, Hoover, AL (US); John Michael Kilpatrick, Helena, AL (US)

(73) Assignee: BIOCRYST PHARMACEUTICALS, INC., Durham, NC (US)

( * ) Notice: Subject to any disclaimer, the term of this patent is extended or adjusted under 35 U.S.C. 154(b) by 189 days.

This patent is subject to a terminal disclaimer.

(21) Appl. No.: 17/382,219

(22) Filed: Jul. 21, 2021

(65) Prior Publication Data

US 2022/0040137 A1 Feb. 10, 2022

Related U.S. Application Data

(60) Continuation of application No. 16/533,283, filed on Aug. 6, 2019, now Pat. No. 11,464,755, which is a continuation of application No. 15/714,918, filed on Sep. 25, 2017, now Pat. No. 10,391,075, which is a continuation of application No. 14/313,738, filed on Jun. 24, 2014, now Pat. No. 9,770,427, which is a continuation of application No. 13/103,562, filed on May 9, 2011, now Pat. No. 8,778,997, which is a division of application No. 11/705,546, filed on Feb. 12, 2007, now abandoned.

(60) Provisional application No. 60/772,748, filed on Feb. 13, 2006.

(51) Int. Cl.

| | |
|---|---|
| ***A61K 31/215*** | (2006.01) |
| ***A61K 9/00*** | (2006.01) |
| ***A61K 31/195*** | (2006.01) |
| ***A61K 31/196*** | (2006.01) |
| ***A61K 45/06*** | (2006.01) |

(52) U.S. Cl.

CPC .......... *A61K 31/215* (2013.01); *A61K 9/0019* (2013.01); *A61K 9/006* (2013.01); *A61K 31/195* (2013.01); *A61K 31/196* (2013.01); *A61K 45/06* (2013.01)

(58) Field of Classification Search

CPC .. A61K 31/215; A61K 9/0019; A61K 31/195; A61K 31/196; A61P 31/16; A61P 31/12

See application file for complete search history.

(56) References Cited

U.S. PATENT DOCUMENTS

| | | | |
|---|---|---|---|
| 5,453,533 | A | 9/1995 | Luo et al. |
| 6,410,594 | B1 | 6/2002 | Babu et al. |
| 6,503,745 | B1 | 1/2003 | Chand et al. |
| 6,562,861 | B1 | 5/2003 | Babu et al. |
| 6,576,786 | B2 | 6/2003 | Abdel-Magid et al. |
| 6,762,316 | B1 | 7/2004 | Chand et al. |
| 8,778,997 | B2 | 7/2014 | Babu et al. |
| 9,770,427 | B2 | 9/2017 | Babu et al. |
| 2004/0062801 | A1 | 4/2004 | Faour et al. |

FOREIGN PATENT DOCUMENTS

| | | | |
|---|---|---|---|
| JP | 2000-505088 | A | 4/2000 |
| JP | 2001-527058 | A | 12/2001 |
| WO | 1997/47194 | A1 | 12/1997 |
| WO | 1999/33781 | A1 | 7/1999 |
| WO | 2001/097792 | A1 | 12/2001 |
| WO | 2007/117241 | A1 | 10/2007 |

OTHER PUBLICATIONS

Luis Barroso, "Efficacy and Tolerability of the Oral Neuraminidase Inhibitor Peramivir in Experimental Human Influenza: Randomized, Controlled Trials for Prophylaxis and Treatment", Antiviral Therapy, 2005 10:8, pp. 901-910.*

Request for The Submission of an Opinion, for Korean Patent Application No. 10-2022-7042429, mailed Feb. 1, 2023, 4 Pages including English Translation.

Request for The Submission of an Opinion, for Korean Patent Application No. 10-2022-7042429, mailed Jun. 12, 2023, 9 Pages including English Translation.

Search Information Statement received for Australian Patent Application No. AU2006341592, mailed on Feb. 27, 2012, 3 pages.

Search Information Statement received for Australian Patent Application No. AU2007215156, mailed on Nov. 14, 2011, 4 pages.

Sidwell, et al, "Peramivir (BCX-1812, RWJ-270201): potential new therapy for influenza," Expert Opinion, Vo. 11(6), Year 2002, pp. 859-869.

Sidwell, et al., "Influence of virus strain, challenge dose and time of therapy initiation on the in vivo influenza inhibitory effects of RWJ-27020," Antiviral Research, vol. 51, Year 2001, pp. 179-187.

Sidwell, et al., "Inhibition of influenza virus infections in immunosuppressed mice with orally administered peramivir (BCX-1812)", Antiviral Research, vol. 60, Year 2003, pp. 17-25.

Sidwell et al., "In Vivo Influenza Virus-Inhibitory Effects of the Cyclopentane Neuraminidase Inhibitor RWJ-270201" Antimicrob Agents & Chemo; vol. 45, Year 2001, pp. 749-757.

Smee, et al., "Cyclopentane neuraminidase inhibitors with potent in vitro anti-influenza virus activities," Antimicrob Chemother., vol. 45(3), Year 2001, pp. 743-748.

Sweet, et al., "Oral Administration of Cyclopentane Neuraminidase Inhibitors Protects Ferrets against Influenza Virus Infection" Antimicrobial Agents and Chemotherapy; vol. 46, No. 4, Apr. 2002, pp. 996-1004.

Wester et al. "Peramivir injection in the treatment of acute influenza: a review of the literature" Infection and drug resistance, vol. 9, Year 2016, pp. 201-214.

(Continued)

*Primary Examiner* — Sahar Javanmard

(74) *Attorney, Agent, or Firm* — Nicholas J. Landau; Maynard Nexsen PC

(57) ABSTRACT

The invention provides unit dosage forms, kits, and methods useful for treating viral infections.

13 Claims, 2 Drawing Sheets

(56) References Cited

OTHER PUBLICATIONS

Written Decision on Registration, for Korean Patent Application No. 10-2018-7005451, mailed Mar. 21, 2019, 4 Pages including English Translation.
Written Decision on Registration, for Korean Patent Application No. 10-2019-7017311, mailed Sep. 16, 2020, 4 Pages including English Translation.
Written Decision on Registration, for Korean Patent Application No. 10-2020-7036259, mailed Mar. 15, 2021, 4 Pages including English Translation.
Written Decision on Registration, for Korean Patent Application No. 10-2021-7018500, mailed Aug. 2, 2021, 4 Pages including English Translation.
Written Decision on Registration, for Korean Patent Application No. 10-2021-7035812, mailed Sep. 1, 2022, 6 Pages including English Translation.
Written Opinion for Japanese Patent Application No. 2013-174479, mailed Oct. 27, 2014, 12 Pages including English Translation.
Written Opinion, for Korean Patent Application No. 10-2008-7022406, mailed Feb. 12, 2014, 19 Pages including English Translation.
Written Opinion, for Korean Patent Application No. 10-2014-7030611, mailed Feb. 1, 2016, 34 Pages including English Translation.
Written Opinion, for Korean Patent Application No. 10-2014-7030611, mailed Jun. 18, 2015, 7 Pages including English Translation.
Written Opinion, for Korean Patent Application No. 10-2016-7030296, mailed Jun. 19, 2017, 58 Pages including English Translation.
Written Opinion, for Korean Patent Application No. 10-2018-7005451, mailed Nov. 1, 2018, 33 Pages including English Translation.
Written Opinion, for Korean Patent Application No. 10-2019-7017311, mailed Jun. 19, 2020, 34 Pages including English Translation.
Written Opinion, for Korean Patent Application No. 10-20217-035812, mailed Jul. 1, 2022, 5 Pages including English Translation.
Written Opinion, for Korean Patent Application No. 10-2022-7042429, mailed Mar. 31, 2023, 5 Pages including English Translation.
Young, et al., "RWJ-270201 (BCX-1812): a novel neuraminidase inhibitor for influenza" Phil. Trans. R. Soc. Lond. B, vol. 356, Year 2001, pp. 1905-1913.
"BioCryst Announces FDA Approval to Initiate Human Testing of Intravenous Peramivir", Evaluate, Pub. Dec. 22, 2005, http://www.evaluategroup.com/Universal/View.aspx?type=Story&id=77209.
"Biocryst Announces Presentation of Peramivir Human Clinical Data at the 46th Annual ICAAC Meeting", BioCryst Pharmaceuticals, Pub. Sep. 29, 2006, https://ir.biocryst.com/news-releases/news-release-details/ biocryst-announces-presentation-peramivir-human-clinical-data.
Ison et al., "A clinical trial of intravenous peramivir compared with oral oseltamivir for the treatment of seasonal influenza in hospitalized adults", Antiviral Therapy, vol. 18, 2013, pp. 651-661.
Bantia, et al., "Comparison of the anti-influenza virus activity of RWJ-270201 with those of oseltamivir and zanamivir" Antimicrob Agents Chemother., vol. 45(4), Year 2001, pp. 1162-1167.
BioCryst reports positive results from a Phase 2 Study of intravenous peramivir for outpatient influenza (2008). 2 Pages.
BioCryst reports preliminary results from a phase II clinical trial of peramivir in subjects with acute influenza (2007). 3 Pages.
Calfee et al. "Safety and Efficacy of Intravenous Zanamivir in Preventing Experimental Human Influenza A Virus Infection", Antimicrobial Agents arid Chemotherapy, vol. 43, No. 7, Year 1999, pp. 1616-1620.
Chand et al., "Comparison of the anti-influenza virus activity of cyclopentane derivatives with oseltamivir and zanamivir in vivo," Bioorganic & Medicinal Chemistry, vol. 13(12), Year 2005, pp. 4071-4077.
Decision of Refusal for Japanese Patent Application No. 2008-554421, mailed Apr. 25, 2013, 2 Pages including English Translation.
Decision of Refusal for Japanese Patent Application No. 2009-505338, mailed Sep. 4, 2012, 2 Pages including English Translation.
Decision of Refusal for Japanese Patent Application No. 2013-174479, mailed Mar. 10, 2015, 6 Pages including English Translation.
European Medicines Agency, "Summary on Compassionate Use for IV Zanamivir," Jun. 23, 2011; pp. 1-28.
European Medicines Agency, "Summary on Compassionate Use for Tamiflu IV" Sep. 27, 2011; pp. 1-32.
Examination report received for Australian Patent Application No. AU2006341592, mailed on Feb. 28, 2012, 3 pages.
Examination report received for Australian Patent Application No. AU2007215156, mailed on Nov. 15, 2011, 4 pages.
Examination report received for Australian Patent Application No. AU2013216632, mailed on Apr. 12, 2016, 4 pages.
Examination report received for Australian Patent Application No. AU2013216632, mailed on Aug. 18, 2015, 4 pages.
Examination report received for Australian Patent Application No. AU2013216632, mailed on Jan. 14, 2019, 2 pages.
Examination report received for Australian Patent Application No. AU2013216632, mailed on May 1, 2019, 3 pages.
Examination report received for Australian Patent Application No. AU2013216632, mailed on Sep. 18, 2018, 2 pages.
Examination report received for Australian Patent Application No. AU2016262644, mailed on Dec. 11, 2018, 3 pages.
Examination report received for Australian Patent Application No. AU2016262644, mailed on Mar. 2, 2018, 3 pages.
Examination report received for Australian Patent Application No. AU2016262644, mailed on Sep. 28, 2018, 3 pages.
Govorkova, et al., "Comparison of efficacies of RWJ-270201, zanamivir, and oseltamivir against H5N1, H9N2 and other avian influenza viruses" Antimicrob Agents Chemoth., vol. 45(10), Oct. 2001, pp. 2723-2732.
Gubareva et al., "Comparison of the Activities of Zanamivir, Oseltamivir, and RWJ-270201 against Clinical Isolates of Influenza Virus and Neuraminidase Inhibitor-Resistant Variants", Antimicrobial Agents and Chemotherapy, vol. 45, No. 12, Dec. 2001, pp. 3403-3408.
International preliminary report on patentability received for International Patent Application No. PCT/US2006/013535, issued on Oct. 14, 2008, 7 pages.
International preliminary report on patentability received for International Patent Application No. PCT/US2007/003755, issued on Aug. 19, 2008, 9 pages.
International Search Report and Written Opinion received for International Patent Application No. PCT/US2006/013535, mailed on Feb. 9, 2007, 8 pages.
International Search Report and Written Opinion received for International Patent Application No. PCT/US2007/003755, mailed on Jul. 4, 2007, 12 pages.
Ison, et al., "A clinical trial of intravenous peramivir compared with oral oseltamivir for the treatment of seasonal influenza in hospitalized adults," Antiviral Therapy , vol. 18, Year 2013, pp. 651-661.
Kandel et al. "Novel strategies for prevention and treatment of influenza," Expert opinion on therapeutic targets, 2005, vol. 9, No. 1, pp. 1-22.
Examination report received for Australian Patent Application No. AU2013216632, mailed on Aug. 1, 2016, 3 pages.
Notice of Final Rejection, for Korean Patent Application No. 10-2008-7022406, mailed Jun. 30, 2014, 5 Pages including English Translation.
Notice of Final Rejection, for Korean Patent Application No. 10-2014-7030611, mailed Jun. 30, 2016, 5 Pages including English Translation.

(56) References Cited

OTHER PUBLICATIONS

Notice of Final Rejection, for Korean Patent Application No. 10-2016-7030296, mailed Oct. 26, 2017, 7 Pages including English Translation.
Notice of Refusal for Japanese Patent Application No. 2008-554421, mailed Oct. 24, 2012, 7 Pages including English Translation.
Notice of Refusal for Japanese Patent Application No. 2009-505338, mailed Mar. 28, 2012, 7 Pages including English Translation.
Notice of Refusal for Japanese Patent Application No. 2013-174479, mailed Aug. 28, 2014, 6 Pages including English Translation.
Notice of Refusal for Japanese Patent Application No. 2013-174479, mailed Jun. 29, 2016, 13 Pages including English Translation.
Notice of Refusal for Japanese Patent Application No. 2015-137495, mailed Jan. 13, 2017, 4 Pages including English Translation.
Notice of Refusal for Japanese Patent Application No. 2015-137495, mailed May 2, 2016, 6 Pages including English Translation.
Office Action received for Canadian Patent Application No. 2642260, mailed on Sep. 14, 2015, 3 Pages.
Office Action received for European Patent Application No. 07750583.2, mailed on Feb. 13, 2009, 5 Pages.
Office Action received for European Patent Application No. 07750583.2, mailed on Oct. 14, 2010, 10 Pages.
Ornjira et al., "On the Lower Susceptibility of Oseltamivir to Influenza Neuraminidase Subtype N1 than Those in N2 and N9", Biophysical Journal, vol. 92, Feb. 2007, pp. 798-807.
Brennan et al., "Safety, Tolerability, and Pharmacokinetics of Intravenous Oseltamivir: Single- and Multiple-Dose Phase I Studies with Healthy Volunteers", Antimicrobial Agents and Chemotherapy, vol. 56, No. 9, Year 2012, pp. 4729-4737.
Request for The Submission of an Opinion, for Korean Patent Application No. 10-2008-7022406 , mailed Aug. 13, 2013, 15 Pages including English Translation.
Request for The Submission of an Opinion, for Korean Patent Application No. 10-2014-7030611, mailed Dec. 18, 2014, 4 Pages including English Translation.
Request for The Submission of an Opinion, for Korean Patent Application No. 10-2014-7030611, mailed Oct. 30, 2015, 9 Pages including English Translation.
Request for The Submission of an Opinion, for Korean Patent Application No. 10-2016-7030296, mailed Dec. 19, 2016, 11 Pages including English Translation.
Request for The Submission of an Opinion, for Korean Patent Application No. 10-2018-7005451, mailed May 1, 2018, 9 Pages including English Translation.
Request for The Submission of an Opinion, for Korean Patent Application No. 10-2019-7017311, mailed May 1, 2018, 9 Pages including English Translation.
Request for The Submission of an Opinion, for Korean Patent Application No. 10-2021-7035812, mailed Jan. 3, 2022, 4 Pages including English Translation.

* cited by examiner

ANTIVIRAL TREATMENTS

RELATED APPLICATIONS

This application is a continuation of U.S. patent application Ser. No. 16/533,283, filed Aug. 6, 2019 (pending). U.S. patent application Ser. No. 16/533,283 is a continuation of U.S. patent application Ser. No. 15/714,918, filed Sep. 25, 2017 (now U.S. Pat. No. 10,391,075, issued Aug. 27, 2019). U.S. application Ser. No. 15/714,918 is a continuation of Ser. No. 14/313,738, filed Jun. 24, 2014 (now U.S. Pat. No. 9,770,427, issued Sep. 26, 2017). U.S. application Ser. No. 14/313,738 is a continuation of Ser. No. 13/103,562, filed May 9, 2011 (now U.S. Pat. No. 8,778,997, issued Jul. 15, 2014). U.S. patent application Ser. No. 13/103,562 is a divisional application of U.S. application Ser. No. 11/705,546, filed Feb. 12, 2007 (abandoned). U.S. application Ser. No. 11/705,546 claims priority to and the benefit of U.S. Application No. 60/772,748, filed Feb. 13, 2006, which applications are herein incorporated by reference.

BACKGROUND

The influenza virus neuraminidase inhibitor peramivir has marked activity against the influenza virus in vitro and in experimentally infected mice (Govorkova et al., *Antimicrobial Agents and Chemotherapy,* 45(10), 2723-2732 (2001); and Smee et al., *Antimicrobial Agents and Chemotherapy,* 45(3), 743-748 (2001)). Unfortunately, clinical trials using this drug showed a suboptimal therapeutic effect on influenza infection in humans following oral administration over a period of days. Currently there is a need for methods and formulations that are useful for treating viral infections (e.g., influenza infections) in humans.

SUMMARY OF THE INVENTION

It has unexpectedly been discovered that a single intravenous administration of peramivir to a mouse is effective to treat influenza. These findings are unexpected not only because of the high effectiveness of a single administration of the compound, but also because of the low dose of the compound that was found to provide effective treatment. The ability to obtain therapeutically useful effects with a single administration is important inter alia because it minimizes patient compliance issues resulting from the need for multiple administrations. Additionally, the administration of a low dose is important because it minimizes cost and the potential for side-effect. It has also been unexpectedly discovered that intravenous and intramuscular injections of peramivir to humans provides high plasma concentrations of peramivir with an extended half-life.

Accordingly, in one embodiment the invention provides a method for treating a viral infection (e.g., an influenza infection) in a human comprising administering an effective anti-viral amount of a compound of formula I, II, III, or IV:

(I)

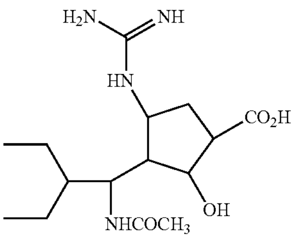

-continued (II)

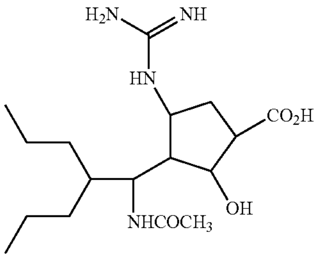

(III)

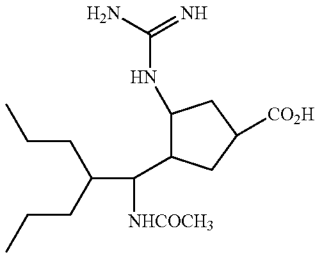

(IV)

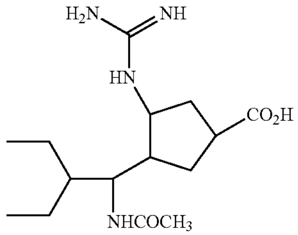

or a pharmaceutically acceptable salt thereof, to the human by an intravenous route.

The invention also provides a method for inhibiting a neuraminidase in a human comprising administering an effective inhibitory amount of a compound of formula I, II, III, or IV, or a pharmaceutically acceptable salt thereof, to the human by an intravenous route.

The invention also provides a unit dosage form that is suitable for intravenous administration to a human comprising up to about 400 mg of a compound of formula I, II, III, or IV, or a pharmaceutically acceptable salt thereof.

The invention also provides a unit dosage form that is suitable for intravenous administration to a human comprising up to about 1,000 mg (e.g., up to about 800, 600, 500, 400, 300, 200, 150, 100, or 75 mg) of a compound of formula I, II, III, or IV, or a pharmaceutically acceptable salt thereof.

The invention also provides a kit comprising packaging materials, a compound of formula I, II, III, or IV, or a pharmaceutically acceptable salt thereof, and instructions for administering the compound to a human by an intravenous route.

The invention also provides the use of a compound of formula I, II, III, or IV, or a pharmaceutically acceptable salt thereof, in the manufacture of a medicament for intravenous injection for increasing life expectancy or reducing mortality in a group of mammals exposed to a source of an influenza virus, by intravenous injection of a dose of the medicament into each member of the group presenting clinical symptoms of infection.

The invention also provides the use of a compound of formula I, II, III, or IV, or a pharmaceutically acceptable salt thereof, in the manufacture of a medicament for intravenous injection for increasing life expectancy or reducing mortality in a group of mammals exposed to a source of an influenza virus, by intravenous injection of a dose of the medicament into each member of the group.

DETAILED DESCRIPTION

Figure 1:
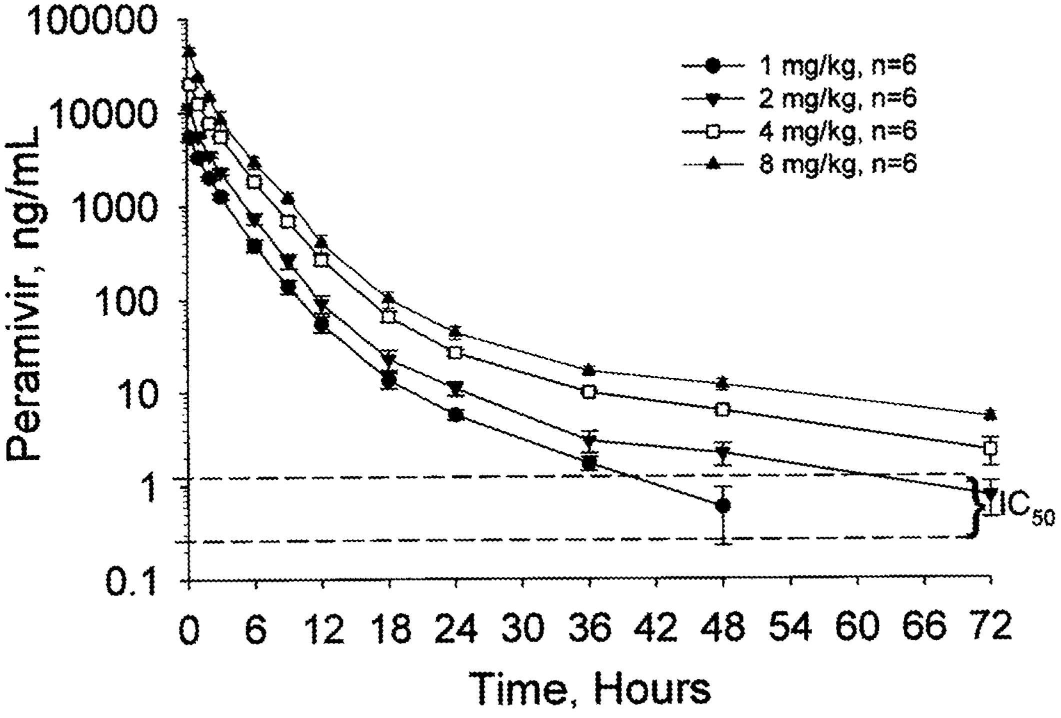
FIG. 1 depicts plasma peramivir concentration time curves after 15 minute intravenous infusions of peramivir to healthy human volunteers.

The influenza virus neuraminidase inhibitor peramivir has been previously shown to have marked activity against influenza virus in vitro and in experimentally infected mice (Govorkova et al., (2001); and Smee et al., (2001)). Unfortunately, clinical trials using this drug showed an inadequate inhibitory effect on influenza in humans. This effect was attributed to a poor adsorption of the drug when administered once daily orally in patients.

It has been discovered that peramivir is well adsorbed when administered intravenously (i.v.) in mice and that the compound remains at relatively high levels in the plasma for at least 6 hours. A series of experiments presented herein indicates that a single treatment of peramivir given i.v. will protect mice infected with an influenza virus.

Accordingly, certain embodiments of the present invention provide a method for treating a viral infection in a human comprising administering an effective anti-viral amount of a compound of formula I, II, III, or IV:

(I)

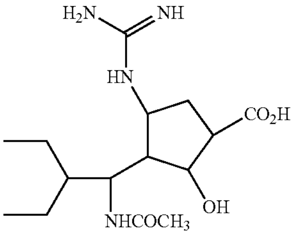

(II)

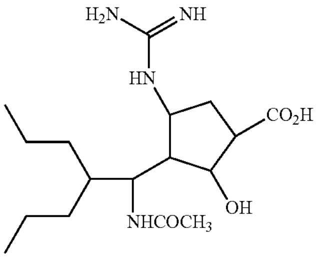

(III)

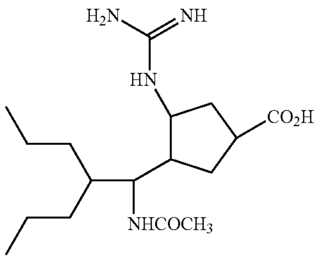

-continued (IV)

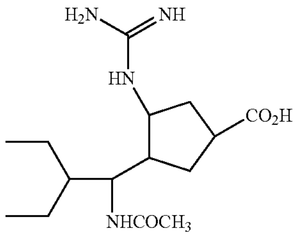

or a pharmaceutically acceptable salt thereof, to the human by an intravenous route.

In certain embodiments, the compound of formula I, II, III, or IV is a compound of formula Ia, IIa, IIIa, or IVa:

(Ia)

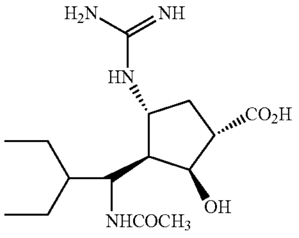

(IIa)

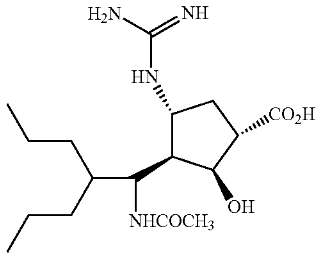

(IIIa)

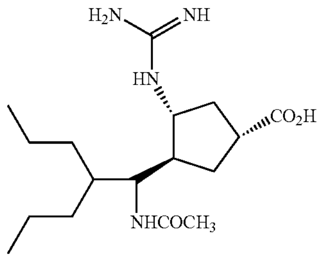

(IVa)

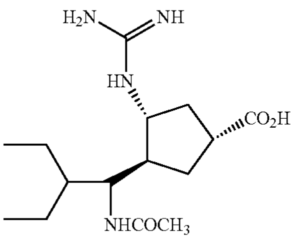

In certain embodiments, the viral infection is an influenza infection. In certain embodiments, the viral infection is an influenza type A or type B infection. In certain embodiments, the viral infection is caused by a strain of virus represented by the formula $H_xN_y$ wherein X is an integer from 1-16 and Y is an integer from 1-9. In certain embodiments, the influenza is an H3N2, H1N1, H5N1, avian, or seasonal influenza In certain embodiments, the effective anti-viral amount is up to about 800 mg. In certain embodiments, the effective anti-viral amount is up to about 400 mg. In certain embodiments, the effective anti-viral amount is up to about 300 mg. In certain embodiments, the effective anti-viral amount is up to about 200 mg.

In certain embodiments, the entire effective dose is administered in one intravenous administration. In certain embodiments, the entire effective dose is administered in multiple intravenous administrations.

In certain embodiments, a compound or formula Ia, or a pharmaceutically acceptable salt thereof, is administered.

In certain embodiments, the plasma concentration of the compound is higher than the $IC_{50}$ of the virus causing the viral infection 12 hours following administration of the compound.

Certain embodiments of the present invention provide a method for inhibiting a neuraminidase in a human comprising administering an effective inhibitory amount of a compound of formula I, II, III, or IV:

(I)

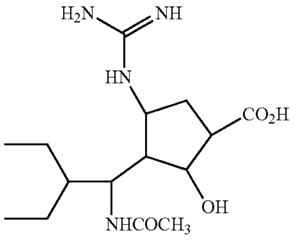

(II)

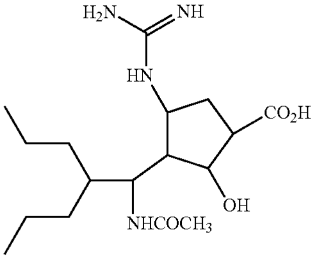

(III)

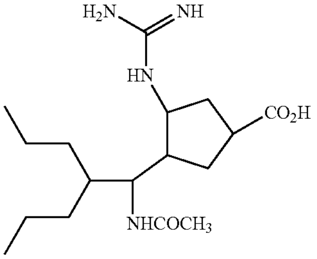

(IV)

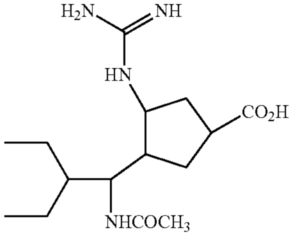

or a pharmaceutically acceptable salt thereof, to the human by an intravenous route.

In certain embodiments, the compound of formula I, II, III, or IV is a compound of formula Ia, IIa, IIIa, or IVa:

(Ia)

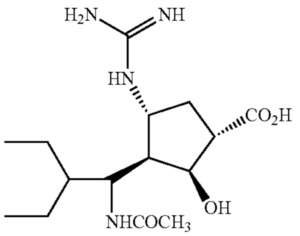

(IIa)

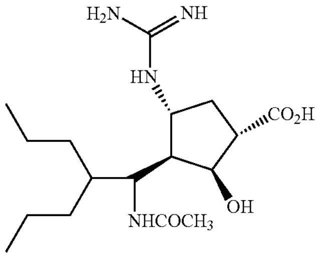

(IIIa)

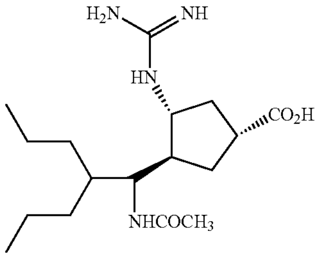

(IVa)

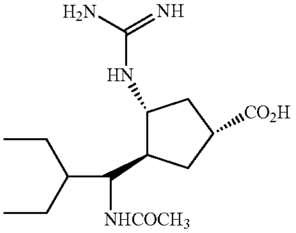

or a pharmaceutically acceptable salt thereof.

In certain embodiments, the effective inhibitory amount is up to about 800 mg. In certain embodiments, the effective inhibitory amount is up to about 400 mg. In certain embodiments, the effective inhibitory amount is up to about 300 mg. In certain embodiments, the effective inhibitory amount is up to about 200 mg.

In certain embodiments, the entire effective inhibitory dose is administered in one intravenous administration. In certain embodiments, the entire effective inhibitory dose is administered in multiple intravenous administrations.

In certain embodiments, a compound of formula Ia, or a pharmaceutically acceptable salt thereof, is administered.

In certain embodiments, the methods may further comprise orally administering a neuraminidase inhibitor to the human.

In certain embodiments, the neuraminidase inhibitor that is administered orally is oseltamivir carboxylate.

In certain embodiments, the neuraminidase inhibitor that is administered orally is a compound of formula I, II, III, or IV:

(I)

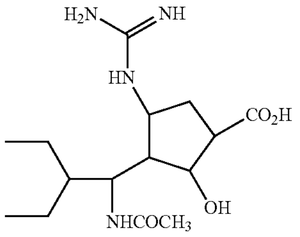

(II)

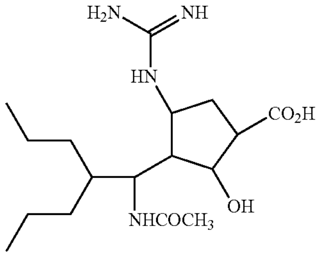

(III)

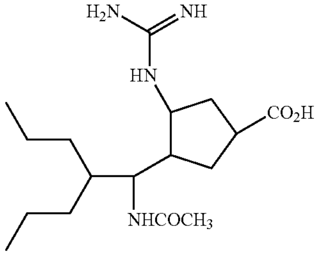

(IV)

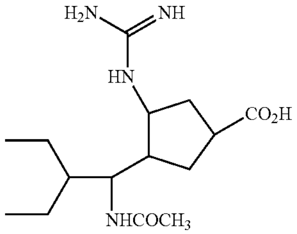

or a pharmaceutically acceptable salt thereof.

In certain embodiments, the neuraminidase inhibitor that is administered orally is a compound of formula Ia, IIa, IIIa, or IVa:

(Ia)

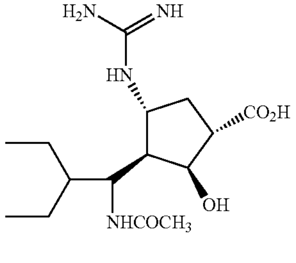

-continued (IIa)

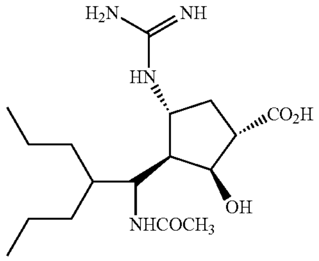

(IIIa)

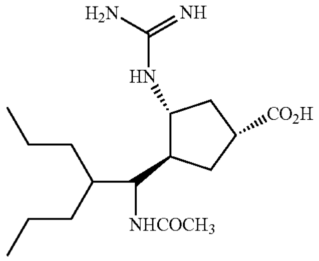

(IVa)

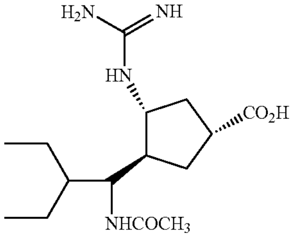

or a pharmaceutically acceptable salt thereof.

In certain embodiments, the neuraminidase inhibitor that is administered orally is a compound of formula Ia, or a pharmaceutically acceptable salt thereof.

In certain embodiments, the neuraminidase inhibitor that is administered orally is administered for up to 20 days. In certain embodiments, the neuraminidase inhibitor that is administered orally is administered for up to 10 days. In certain embodiments, the neuraminidase inhibitor that is administered orally is administered for up to 5 days.

Certain embodiments of the present invention provide a unit dosage form that is suitable for intravenous administration to a human, comprising up to about 800 mg of a compound of formula I, II, III, or IV:

(I)

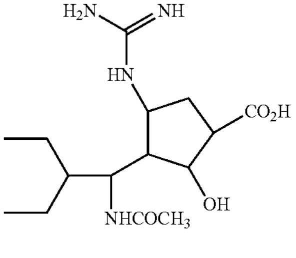

-continued (II)

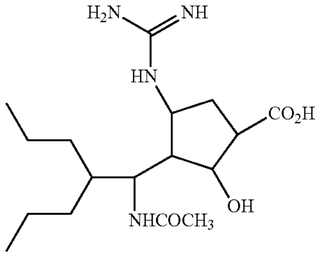

(III)

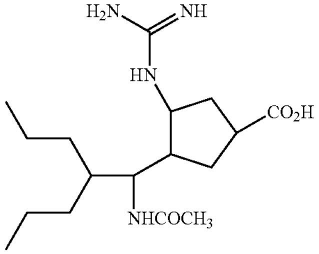

(IV)

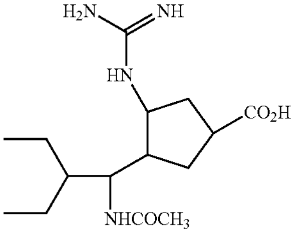

or a pharmaceutically acceptable salt thereof.

In certain embodiments, the compound of formula I, II, III, or IV is a compound of formula Ia, IIa, IIIa, or IVa:

(Ia)

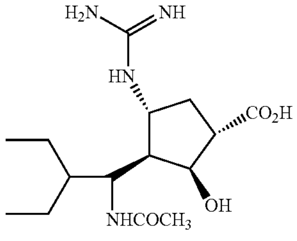

(IIa)

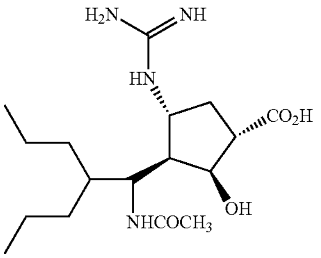

-continued (IIIa)

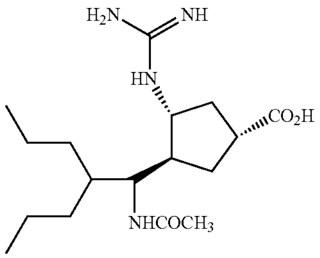

(IVa)

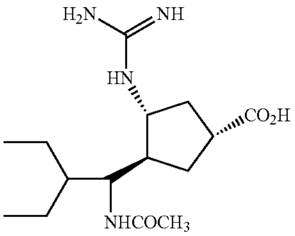

or a pharmaceutically acceptable salt thereof.

In certain embodiments, the unit dosage form comprises up to about 400 mg of the compound or salt. In certain embodiments, the unit dosage form comprises up to about 300 mg of the compound or salt. In certain embodiments, the unit dosage form comprises up to about 200 mg of the compound or salt.

Certain embodiments of the present invention provide a kit, comprising packaging materials, a compound of formula I, II, III, or IV:

(I)

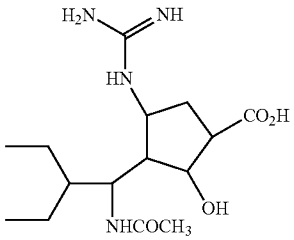

(II)

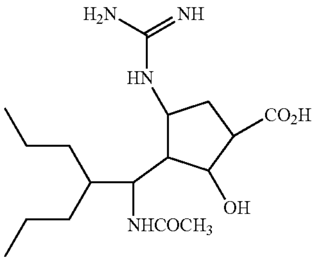

(III)

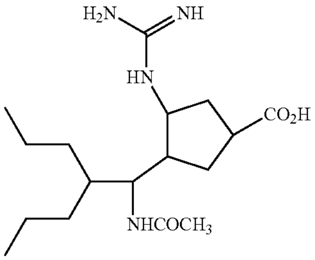

-continued (IV)

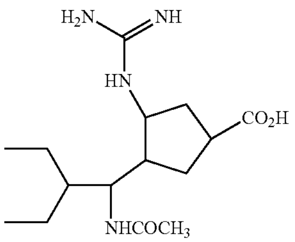

or a pharmaceutically acceptable salt thereof, and instructions for administering the compound to a human by an intravenous route.

In certain embodiments, the compound is provided in a formulation suitable for intravenous administration.

In certain embodiments, the kit comprises up to about 800 mg of the compound or salt. In certain embodiments, the kit comprises up to about 400 mg of the compound or salt. In certain embodiments, the kit comprises up to about 300 mg of the compound or salt. In certain embodiments, the kit comprises up to about 200 mg of the compound or salt.

Certain embodiments of the present invention provide a kit comprising packaging materials, a unit dosage form as described herein, and instructions for administering the compound to a human by an intravenous route.

Certain embodiments of the present invention provide a use of a compound of formula I, II, III, or IV:

(I)

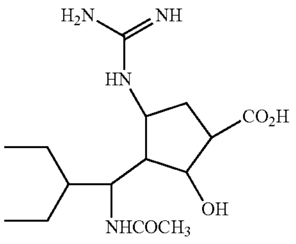

(II)

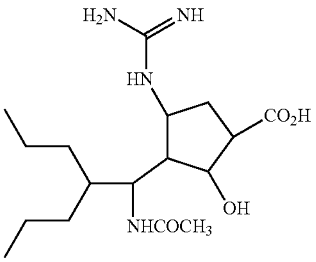

(III)

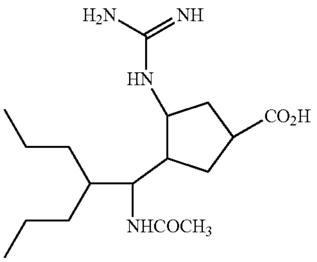

-continued (IV)

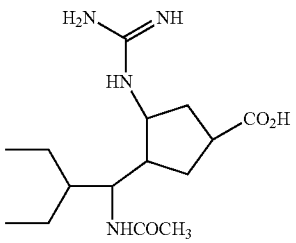

or a pharmaceutically acceptable salt thereof, in the manufacture of a medicament for intravenous injection for increasing life expectancy or reducing mortality in a group of mammals exposed to a source of an influenza virus, by intravenous injection of a dose of the medicament into each member of the group presenting clinical symptoms of infection.

In certain embodiments, the compound of formula I, II, III, or IV is a compound of formula Ia, IIa, IIIa, or IVa:

(Ia)

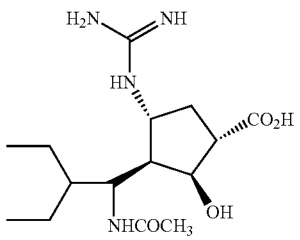

(IIa)

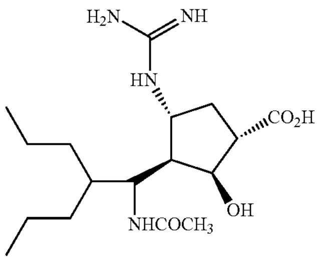

(IIIa)

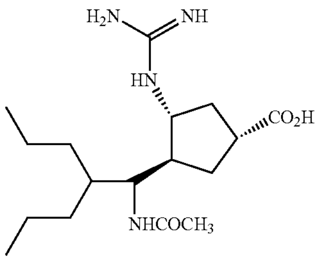

(IVa)

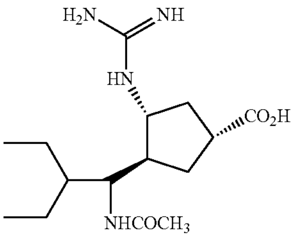

or a pharmaceutically acceptable salt thereof.

In certain embodiments, the influenza virus is an avian influenza virus. In certain embodiments, the influenza virus is an influenza type A or type B virus. In certain embodiments, the influenza virus is H5NI, or a mutant strain thereof. In certain embodiments, the influenza virus is a strain of virus represented by the formula $H_xN_y$ wherein X is an integer from I-I 6 and Y is an integer from 1-9. In certain embodiments, the influenza virus is an H3N2, H1N1, H5N1, avian, or seasonal influenza virus.

In certain embodiments, each member of the group presenting symptoms of infection receives only one intravenous dose of the medicament. In certain embodiments, each member of the group presenting symptoms of infection receives multiple intravenous doses of the medicament.

In certain embodiments, the members of the group presenting clinical symptoms of infection are treated orally with a neuraminidase inhibitor. In certain embodiments, the neuraminidase inhibitor is oseltamivir carboxylate. In certain embodiments, the neuraminidase inhibitor is a compound of formula I, II, III, or IV:

(I)

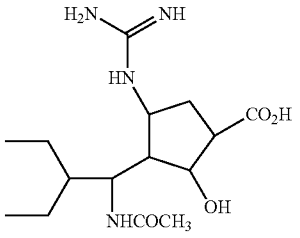

(II)

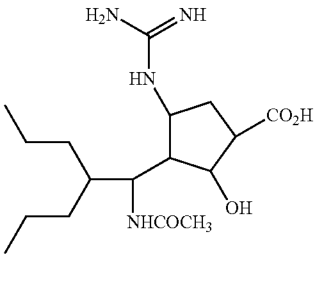

(III)

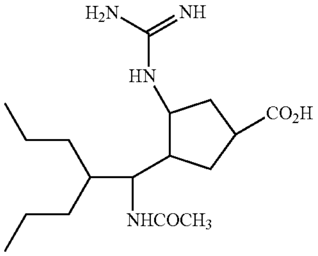

(IV)

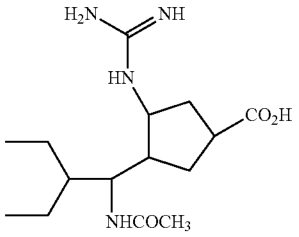

or a pharmaceutically acceptable salt thereof.

In certain embodiments, the neuraminidase inhibitor is a compound of formula Ia, IIa, IIIa, or IVa:

(Ia)

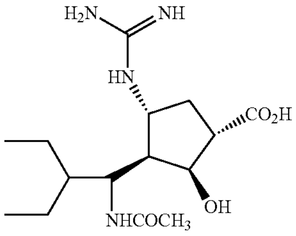

(IIa)

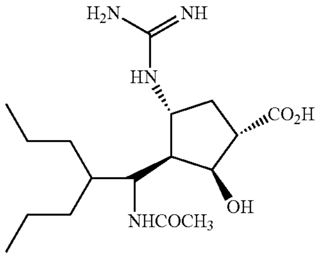

(IIIa)

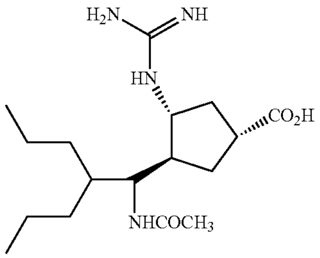

(IVa)

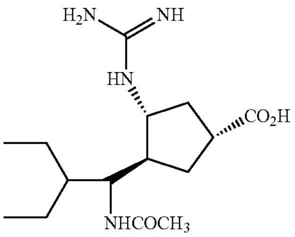

or a pharmaceutically acceptable salt thereof. In certain embodiments, the neuraminidase inhibitor is a compound of formula Ia, or a pharmaceutically acceptable salt thereof.

In certain embodiments, the source of the virus is an infected bird. In certain embodiments, the source of the virus is a mammal presenting symptoms of infection.

In certain embodiments, the use is for reducing mortality.

Certain embodiments of the present invention provide a use of a compound of formula I, II, III, or IV:

(I)

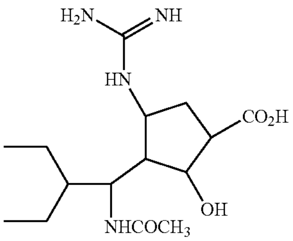

-continued (II)

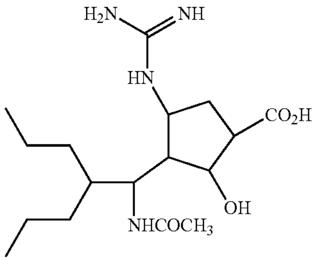

(III)

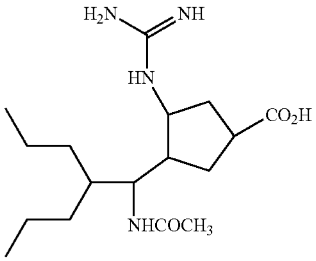

(IV)

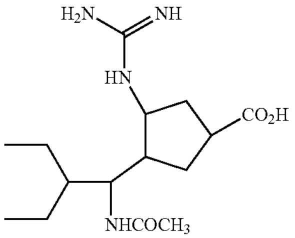

or a pharmaceutically acceptable salt thereof, in the manufacture of a medicament for intravenous injection for increasing life expectancy or reducing mortality in a group of mammals exposed to a source of an influenza virus, by intravenous injection of a dose of the medicament into each member of the group.

In certain embodiments, the compound of formula I, II, III, or IV is a compound of formula Ia, IIa, IIIa, or IVa:

(Ia)

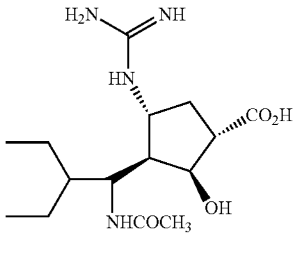

(IIa)

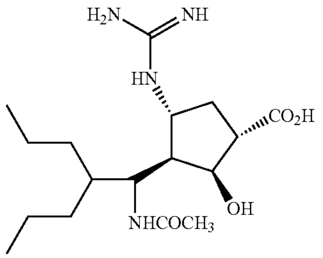

-continued (IIIa)

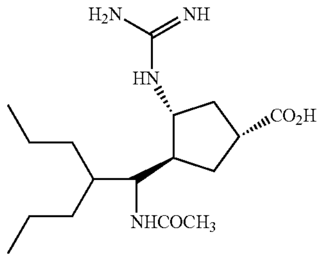

(IVa)

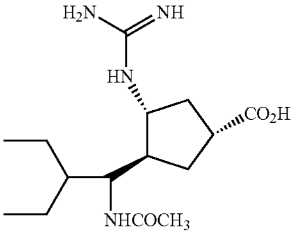

or a pharmaceutically acceptable salt thereof.

In certain embodiments, the influenza virus is an avian influenza virus. In certain embodiments, the avian influenza virus is H5N1, or a mutant strain thereof. In certain embodiments, the influenza virus is a strain of virus represented by the formula $H_xN_y$, wherein X is an integer from 1-16 and Y is an integer from 1-9. In certain embodiments, the influenza virus is an influenza type A or type B virus. In certain embodiments, the influenza virus is an H3N2, H1N1, H5N1, avian, or seasonal influenza virus.

In certain embodiments, each member of the group receives only one intravenous dose of the medicament. In certain embodiments, each member of the group receives multiple intravenous doses of the medicament.

In certain embodiments, the members of the group are treated orally with a neuraminidase inhibitor. In certain embodiments, the neuraminidase inhibitor is oseltamivir carboxylate. In certain embodiments, the neuraminidase inhibitor is a compound of formula I, II, III, or IV:

(I)

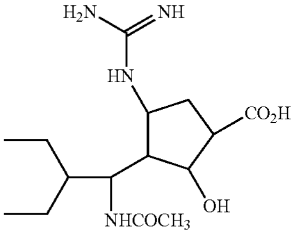

(II)

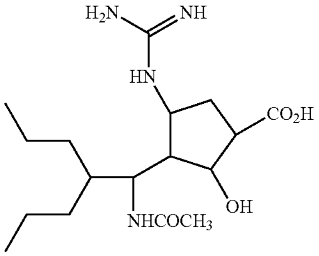

-continued (III)

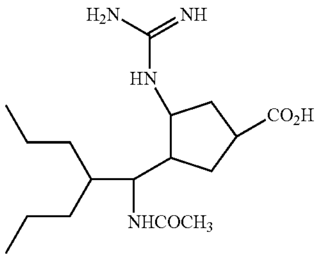

(IV)

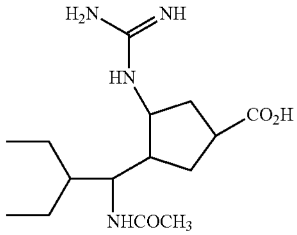

or a pharmaceutically acceptable salt thereof. In certain embodiments, the neuraminidase inhibitor is a compound of formula Ia, IIa, IIIa, or IVa:

(Ia)

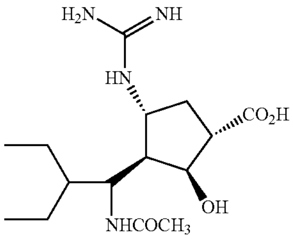

(IIa)

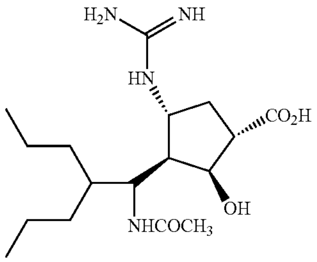

(IIIa)

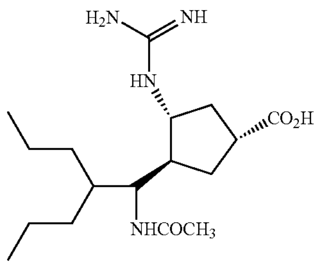

-continued (IVa)

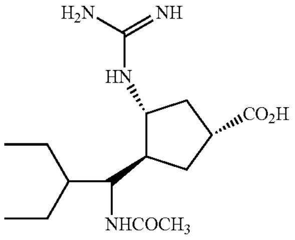

or a pharmaceutically acceptable salt thereof. In certain embodiments, the neuraminidase inhibitor is a compound of formula Ia, or a pharmaceutically acceptable salt thereof. In certain embodiments, the source of the virus is an infected bird. In certain embodiments, the source of the virus is a mammal presenting symptoms of infection.

In certain embodiments, the use is for reducing mortality.

Certain embodiments of the present invention provide a use of a compound of formula I, II, III, or IV:

(I)

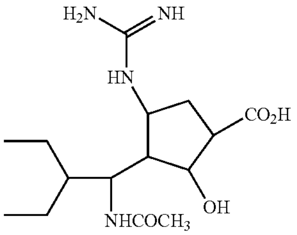

(II)

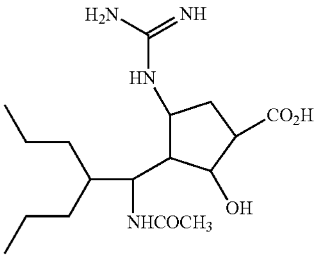

(III)

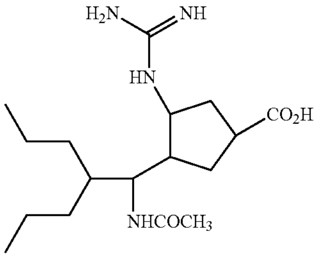

(IV)

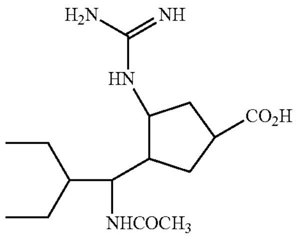

or a pharmaceutically acceptable salt thereof, in the manufacture of a medicament for intravenous injection for achieving a plasma concentration in a human of the compound that is effective to treat a virus by intravenous injection of a dose of the medicament into the human.

Certain embodiments of the present invention provide a use of a compound of formula I, II, III, or IV:

(I)

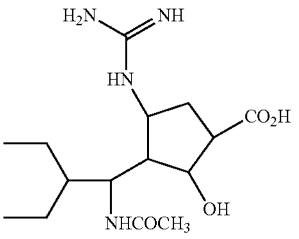

(II)

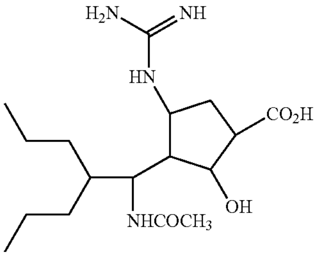

(III)

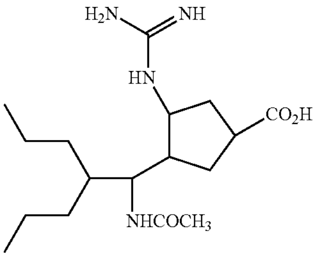

(IV)

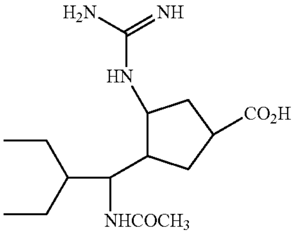

or a pharmaceutically acceptable salt thereof, in the manufacture of a medicament for intramuscular injection for achieving a plasma concentration in a human of the compound that is effective to treat a virus by intramuscular injection of a dose of the medicament into the human.

In certain embodiments, the plasma concentration of the compound is higher than the $IC_{50}$ of the virus 12 hours following injection of the compound.

Mice infected with influenza A/Duck/MN/1525/81 (H5N1) virus were treated a single time i.v. 1 hour pre-virus exposure with peramivir at doses of 20, 10 and 3 mg/kg. Peramivir was significantly protective to the mice at the two highest dosages used, as seen by prevention of deaths, lessening of lung consolidation, and inhibition of lung virus titers. The 3 mg/kg dose was moderately inhibitory to lung parameters. The compound appeared well tolerated in concomitantly run toxicity controls. These data indicate that a single i.v. peramivir treatment is efficacious in influenza virus-infected mice.

The compounds used in the invention are known in the art and can be synthesized by the art worker using available methods (see, e.g., U.S. Pat. No. 6,562,861).

Specific values listed herein for radicals, substituents, and ranges, are for illustration only; they do not exclude other defined values or other values within defined ranges for the radicals and substituents A specific compound of formula I, II, III, or IV is a compound of formula Ia, IIa, IIIa, or IVa:

(Ia)

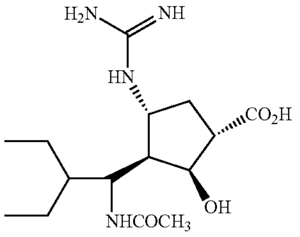

(IIa)

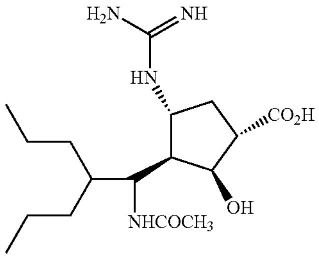

(IIIa)

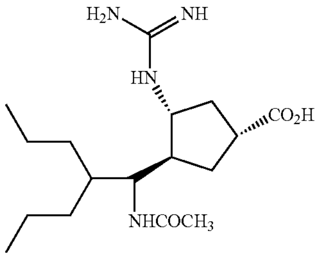

(IVa)

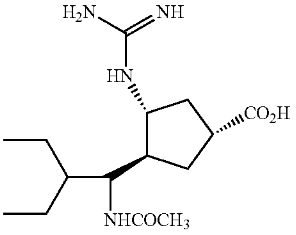

or a pharmaceutically acceptable salt thereof.

A specific compound of formula I, II, III, or IV is (1S,2S,3R,4R)-3-(1-Acetamido-2-ethylbutyl)-4-guanidino-2-hydroxycyclopentane-carboxylic acid; (1S,2S,3R,4R)-3-(1-Acetamido-2-propylpentyl)-4-guanidino-2-hydroxycyclopentanecarboxylic acid; (1R,3R,4R)-3-(1-Acetamido-2-propylpentyl)-4-guanidinocyclopentanecarboxylic acid; or (1R,3R,4R)-3-(1-Acetamido-2-ethylbutyl)-4-guanidinocyclopentanecarboxylic acid; or a pharmaceutically acceptable salt thereof.

A specific compound of formula I is a compound of formula Ia, or a pharmaceutically acceptable salt thereof.

It will be appreciated by those skilled in the art that compounds having one or more chiral centers may exist in and be isolated in optically active and racemic forms. Some compounds may exhibit polymorphism. It is to be understood that the present invention encompasses the use of any racemic, optically-active, polymorphic, or stereoisomeric form, or mixtures thereof, of a compound of formula I, II, III, or IV, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-viral (e.g. anti-influenza) activity using the standard tests described herein, or using other similar tests which are well known in the art.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, phosphate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. The compounds of formula I, II, III, and IV can be formulated as pharmaceutical compositions and administered to a mammalian host, such as a human patient, by intravenous routes. Solutions of the active compound or its salts can be prepared in water, optionally mixed with a nontoxic surfactant. Dispersions can also be prepared in glycerol; liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient(s) which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound(s) into an appropriate solvent with the other optional ingredients enumerated above, optionally followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

As used herein the terms "treat", "treating" and "treatment" include administering a compound prior to the onset of clinical symptoms of a disease state/condition so as to prevent the development of any symptom, as well as administering a compound after the onset of one or more clinical symptoms of a disease state/condition so as to reduce or eliminate any such symptom, aspect or 10 characteristic of the disease state/condition. Such treating need not be absolute to be useful. As illustrated hereinbelow, the active compounds can be administered prior to exposure to the virus. The agents can also be administered subsequent (e.g., within 1, 2, 3, 4, or 5 days) to exposure to the virus.

As used herein the term "unit dosage form" relates to an intravenous formulation containing a specific amount of a drug, the whole of which is intended to be administered as a single dose. It is distinguished from a supply of an indefinite amount of a medicament, e.g., a bottle of medicine, from which a dose has to be measured out.

In one embodiment the invention provides a method for treating a viral infection in a human comprising administering an effective amount of a compound of formula I, II, III, or IV, or a pharmaceutically acceptable salt thereof, to the human by intravenous administration. Typically, the effective amount is administered in a single intravenous administration. In some embodiments, the effective amount is administered in multiple administrations. Accordingly, the methods of the invention provide for high patient compliance and they require a low dose of the effective agent.

In one embodiment of the invention, the effective inhibitory amount of the compound of formula I, II, III, or IV is up to about 1,000 mg.

In one embodiment of the invention, the effective inhibitory amount of the compound of formula I, II, III, or IV is up to about 800 mg.

In one embodiment of the invention, the effective inhibitory amount of the compound of formula I, II, III, or IV is up to about 600 mg.

In one embodiment of the invention, the effective inhibitory amount of the compound of formula I, II, III, or IV is up to about 500 mg.

In one embodiment of the invention, the effective inhibitory amount of the compound of formula I, II, III, or IV is up to about 400 mg.

In one embodiment of the invention, the effective inhibitory amount of the compound of formula I, II, III, or IV is up to about 300 mg.

In one embodiment of the invention, the effective inhibitory amount of the compound of formula I, II, III, or IV is up to about 200 mg.

In one embodiment of the invention, the effective inhibitory amount of the compound of formula I, II, III, or IV is up to about 150 mg.

In one embodiment of the invention, the effective inhibitory amount of the compound of formula I, II, III, or IV is up to about 75 mg.

According to the methods of the invention a compound of formula I, II, III, or IV is administered to a human intravenously. In one embodiment of the invention, the compound of formula I, II, III, or IV is administered once to a human intravenously. In another embodiment of the invention, a neuraminidase inhibitor is also administered to the human orally. In one embodiment of the invention, the neuraminidase inhibitor that is administered orally is oseltamivir carboxylate. In one embodiment of the invention, the neuraminidase inhibitor that is administered orally is a compound of formula I, II, III, or IV:

(I)

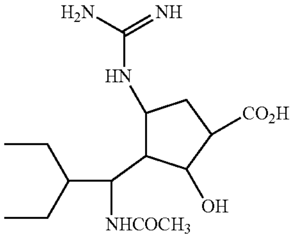

(II)

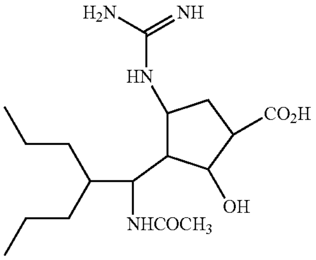

(III)

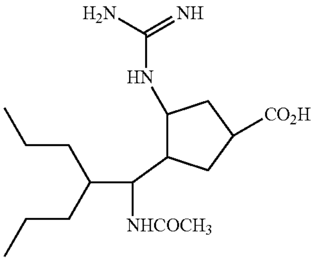

(IV)

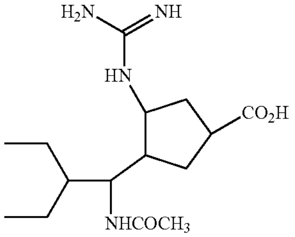

or a pharmaceutically acceptable salt thereof. In one embodiment of the invention, the neuraminidase inhibitor that is administered orally is a compound of formula Ia, IIa, IIIa, or IVa:

(Ia)

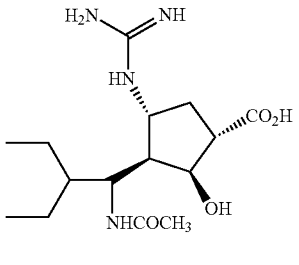

-continued (IIa)

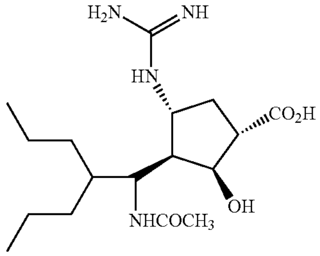

(IIIa)

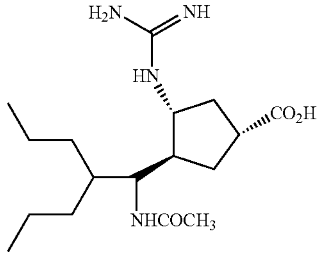

(IVa)

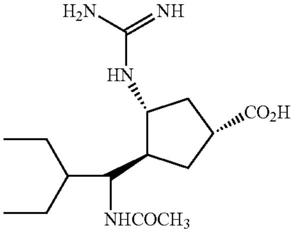

or a pharmaceutically acceptable salt thereof. In one embodiment of the invention, the neuraminidase inhibitor that is administered orally is a compound of formula Ia, or a pharmaceutically acceptable salt thereof.

According to the methods of the invention, the compound of formula I, II, III, or IV, or a pharmaceutically acceptable salt thereof, can also be administered in combination with one or more additional therapeutic agents, such as anti-viral agents (e.g., agents active against influenza) or antibiotics.

The intravenous formulations of the invention can also comprise one or more additional therapeutic agents, such as anti-viral agents (e.g., agents active against influenza) and antibiotics.

Thus, intravenous administration of peramivir to treat a viral infection is described herein. Intramuscular administration of peramivir to treat a viral infection is also described herein (see, e.g., Example 2), which further exemplifies intramuscular administration of peramivir to treat a viral infection, as is described in International Application No. PCT/US2006/013535, filed Apr. 12, 2006, the disclosure of which is incorporated by reference. Further, as described herein, it has been unexpectedly discovered that intravenous and intramuscular injections of peramivir to humans provides high plasma concentrations of peramivir with an extended plasma half-life.

As described herein, the compounds described herein can be used to treat a virus, e.g., an influenza virus. For example 1 the compounds can be used to treat any one or combination of the following strains. In the table below, the "H" stands for a type of hemagglutinin, and the "N" stands for a type of neuraminidase. The formula HxNy wherein X is an integer from 1-16 and Y is an integer from 1-9, can also be used to describe the combinations presented in the table.

TABLE 1

| | N1 | N2 | N3 | N4 | N5 | N6 | N7 | N8 | N9 |
|---|---|---|---|---|---|---|---|---|---|
| H1 | H1N1 | H1N2 | H1N3 | H1N4 | H1N5 | H1N6 | H1N7 | H1N8 | H1N9 |
| H2 | H2N1 | H2N2 | H2N3 | H2N4 | H2N5 | H2N6 | H2N7 | H2N8 | H2N9 |
| H3 | H3N1 | H3N2 | H3N3 | H3N4 | H3N5 | H3N6 | H3N7 | H3N8 | H3N9 |
| H4 | H4N1 | H4N2 | H4N3 | H4N4 | H4N5 | H4N6 | H4N7 | H4N8 | H4N9 |
| H5 | H5N1 | H5N2 | H5N3 | H5N4 | H5N5 | H5N6 | H5N7 | H5N8 | H5N9 |
| H6 | H6N1 | H6N2 | H6N3 | H6N4 | H6N5 | H6N6 | H6N7 | H6N8 | H6N9 |
| H7 | H7N1 | H7N2 | H7N3 | H7N4 | H7N5 | H7N6 | H7N7 | H7N8 | H7N9 |
| H8 | H8N1 | H8N2 | H8N3 | H8N4 | H8N5 | H8N6 | H8N7 | H8N8 | H8N9 |
| H9 | H9N1 | H9N2 | H9N3 | H9N4 | H9N5 | H9N6 | H9N7 | H9N8 | H9N9 |
| H10 | H10N1 | H10N2 | H10N3 | H10N4 | H10N5 | H10N6 | H10N7 | H10N8 | H10N9 |
| H11 | H11N1 | H11N2 | H11N3 | H11N4 | H11N5 | H11N6 | H11N7 | H11N8 | H11N9 |
| H12 | H12N1 | H12N2 | H12N3 | H12N4 | H12N5 | H12N6 | H12N7 | H12N8 | H12N9 |
| H13 | H13N1 | H13N2 | H13N3 | H13N4 | H13N5 | H13N6 | H13N7 | H13N8 | H13N9 |
| H14 | H14N1 | H14N2 | H14N3 | H14N4 | H14N5 | H14N6 | H14N7 | H14N8 | H14N9 |
| H15 | H15N1 | H15N2 | H15N3 | H15N4 | H15N5 | H15N6 | H15N7 | H15N8 | H15N9 |
| H16 | H16N1 | H16N2 | H16N3 | H16N4 | H16N5 | H16N6 | H16N7 | H16N8 | H16N9 |

The virus may be, for example, an avian virus or a humanized avian virus. Thus, the term “avian virus” includes both avian forms of the virus and humanized forms of the avian virus.

Certain embodiments of the present invention provide the use of a compound of formula I, II, III, or IV:

(I)

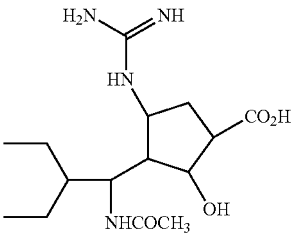

(II)

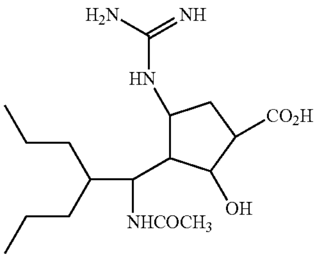

(III)

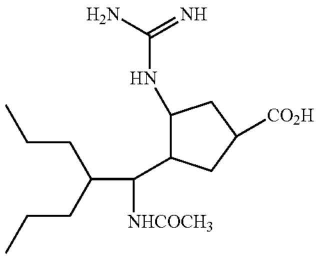

-continued (IV)

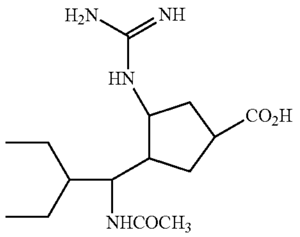

or a pharmaceutically acceptable salt thereof, in the manufacture of a medicament for intravenous injection for achieving a plasma concentration in a human of the compound that is effective to treat a virus by intravenous injection of a dose of the medicament into the human.

Certain embodiments of the present invention also provide the use of a compound of formula I, II, III, or IV:

(I)

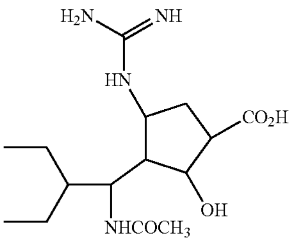

(II)

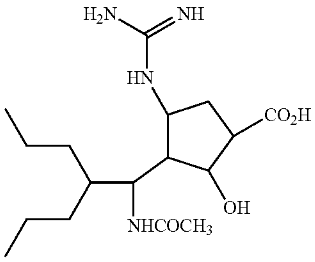

-continued (III)

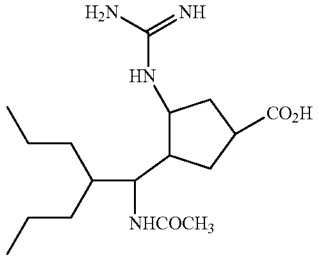

(IV)

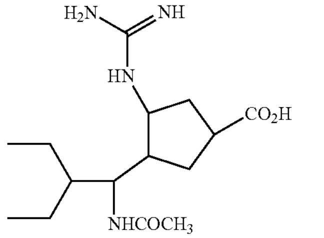

or a pharmaceutically acceptable salt thereof, in the manufacture of a medicament for intramuscular injection for achieving a plasma concentration in a human of the compound that is effective to treat a virus by intramuscular injection of a dose of the medicament into the human.

Certain embodiments of the invention also provide compositions comprising peramivir formulated for intravenous administration to a human. Certain embodiments of the invention also provide compositions comprising peramivir formulated for intravenous administration for use in treating a virus by achieving a plasma concentration in a human of peramivir that is effective to treat the virus. Certain embodiments of the invention also provide compositions comprising peramivir formulated for intramuscular administration to a human. Certain embodiments of the invention also provide compositions comprising peramivir formulated for intramuscular administration for use in treating a virus by achieving a plasma concentration in a human of peramivir that is effective to treat the virus.

In certain embodiments of the invention, the plasma concentration of the compound is higher than the $IC_{50}$ of the virus at least about 12 hours following the injection.

In certain embodiments of the invention, the plasma concentration of the compound is higher than the $IC_{50}$ of the virus at least about 24 hours following the injection.

In certain embodiments of the invention, the plasma concentration of the compound is higher than the $IC_{50}$ of the virus at least about 36 hours following the injection.

In certain embodiments of the invention, the plasma concentration of the compound is higher than the $IC_{50}$ of the virus at least about 48 hours following the injection.

In certain embodiments of the invention, the plasma concentration of the compound is higher than the $IC_{50}$ of the virus at least about 60 hours following the injection.

In certain embodiments of the invention, the plasma concentration of the compound is higher than the $IC_{50}$ of the virus at least about 72 hours following the injection.

In certain embodiments of the invention, the virus is an influenza virus. In certain embodiments of the invention, the virus is an avian influenza virus. In certain embodiments of the invention, the virus is H5N1, or a mutant strain thereof.

The invention will now be illustrated by the following non-limiting Examples.

Example 1. Effect of IV Treatment with Peramivir on Influenza A Virus Infection Experiment Design: Mice were infected i.n. with a dose thought to be the LD100 of influenza virus. Groups of 10 mice were treated i.v. with peramivir at dosages of 20, 10 and 3 mg/kg a single time 1 hour pre-virus exposure. Placebo (sterile saline) was administered i.v. in parallel with the above to 20 infected mice. Drug-treated infected mice and placebo-treated controls were observed daily for death through 21 days. As toxicity controls, 3 uninfected mice were treated with the highest dose of the compounds in parallel to the infected animals. All toxicity controls were observed for death through 21 days and were weighed immediately prior to the initial treatment and 18 h after the final treatment. Five normal controls were weighed.

TABLE 2

Effect of Single I.V. Treatment with Peramivir on an Influenza A Virus Infection in Mice.
Animals: Female 18-21 gram BALB/c mice
Virus: Influenza A/Duck/MN/152518 (H5N1)
Drug Diluent: Sterile Saline
Treatment Schedule: Peramivir: Single treatment 1 hour pre-virus exposure
Treatment route: Peramivir I.V.;
Expt. duration: 21 days

| | | Tox | Infected, Treated Mice | |
|---|---|---|---|---|
| Treatment | Dose (mg/kg) | Controls Surv/Total | Surv/Total | Mean Day to Death[b] ± SD |
| Peramivir | 20 | 3/3 | 10/10** | >21 ± 0.0*** |
| | 10 | 3/3 | 10/10** | >21 ± 0.0*** |
| | 3 | 3/3 | 5/10 | 9.6 ± 3.1 |
| Saline | — | — | 9/20 | 9.1 ± 1.4 |
| Normal Controls | — | 5/5 | — | — |

[b]Mean day to death of mice dying prior to day 21.
P < 0.01; *P < 0.001 compared to saline-treated controls.

The infection induced in this experiment was lethal to 55% of the mice (Table 1), with a mean day to death of 9.1 days. The single i.v. injection with peramivir at 20 and 10 mg/kg was highly protective to the infected animals, with 100% surviving the infection (P<0.001). Toxicity controls run in parallel all survived and gained weight, indicating compound was well tolerated in this experiment.

These data indicate that peramivir is a significant influenza inhibitor when used in a single i.v. injection.

Example 2. Effects of IV and IM Treatment with Peramivir in Humans

Figure 2:
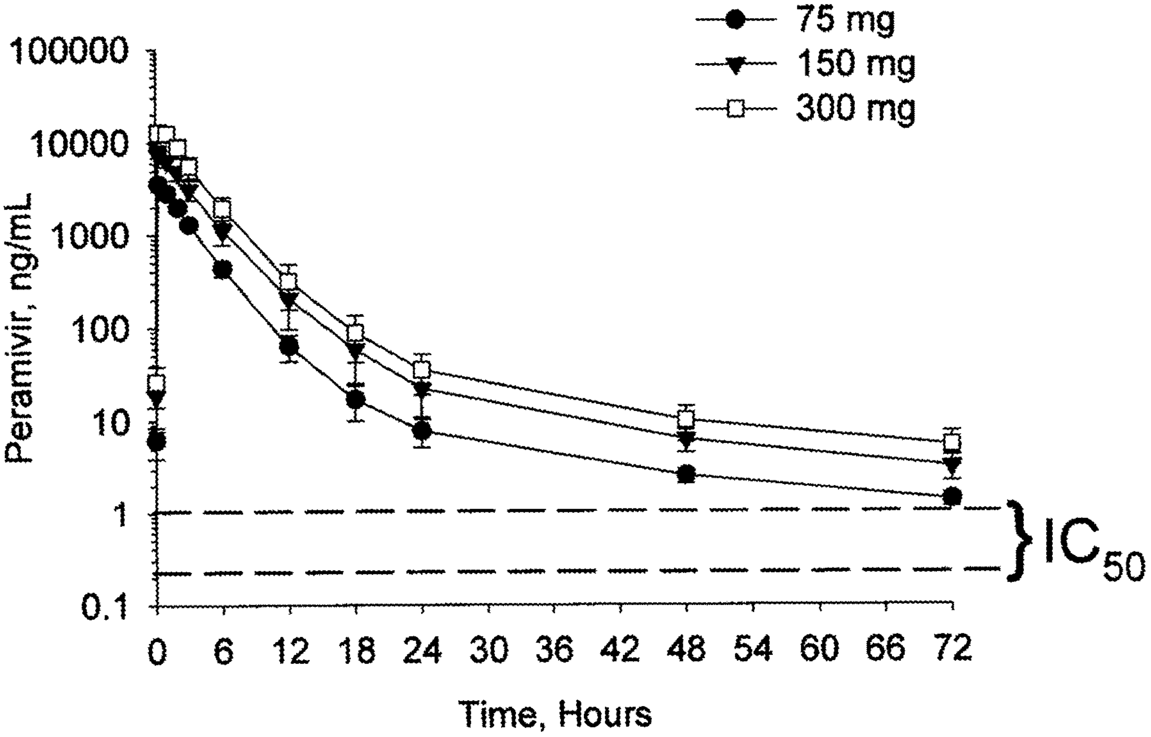
FIG. 2 depicts plasma peramivir concentration time curves after intramuscular injections of peramivir to healthy human volunteers.

Peramivir was studied in a placebo-controlled phase I clinical study in healthy human volunteers to evaluate safety and pharmacokinetic parameters using intravenous and intramuscular administrations. Blood samples were collected from the subjects at different time points after drug administration to determine the concentration of the drug in plasma. The time course plots are shown in FIG. 1 and FIG. 2 for intravenous and intramuscular administrations respectively.

In the intravenous study, peramivir concentrations followed linear kinetics with an unusually extended plasma half life of greater than 12 hours. At doses of 2 mg/kg and above, the level of peramivir in plasma at 48 hours post-dose is greater than the $IC_{50}$ for all strains of influenza virus tested, including H5 virus types. For doses greater than 4 mg/kg, even at 72 hours, the levels of the drug are greater than the $IC_{50}$ values.

In the intramuscular study, peramivir concentrations also followed linear kinetics with an unusually extended plasma half life. Even at 72 hours post-dosing, the levels of peramivir are higher than the $IC_{50}$ values for all the influenza virus strains tested.

The long plasma half-life and the high levels of peramivir in human volunteers are unusual and unexpected findings and indicate that intravenous and intramuscular administrations of peramivir are beneficial in the treatment of influenza in humans.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such As") provided herein, is intended merely to better illuminate the invention and does not pose a limitation on the scope of the invention unless otherwise claimed.

What is claimed is:

1. A method for treating an influenza viral infection in a human comprising administering in multiple intravenous administrations for up to 20 days, the multiple intravenous administrations providing an effective anti-viral amount of from 500 mg to 1,000 mg of a compound of formula I or formula Ia:

I

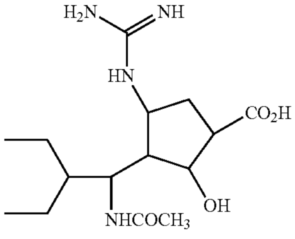

Ia

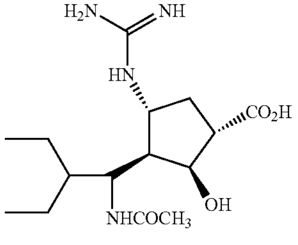

or a pharmaceutically acceptable salt thereof, to the human, wherein the influenza viral infection is a seasonal influenza viral infection.

2. The method of claim 1, wherein the compound of formula I is a compound of formula Ia:

Ia

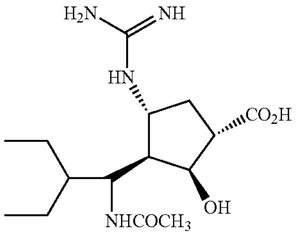

or a pharmaceutically acceptable salt thereof.

3. The method of claim 1, wherein the effective anti-viral amount is 500 mg.

4. The method of claim 1, wherein the effective anti-viral amount is 1000 mg.

5. The method of claim 1, wherein the effective anti-viral amount is 600 mg.

6. The method of claim 1, further comprising orally administering a neuraminidase inhibitor to the human.

7. The method of claim 6, wherein the neuraminidase inhibitor that is administered orally is oseltamivir carboxylate.

8. The method of claim 6, wherein the neuraminidase inhibitor that is administered orally is a compound of formula I, II, III, or IV:

(I)

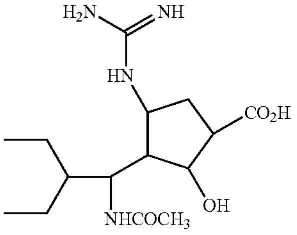

(II)

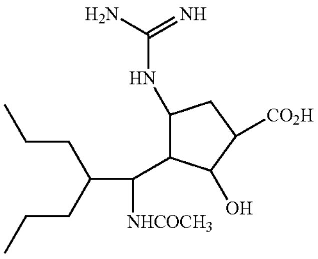

(III)

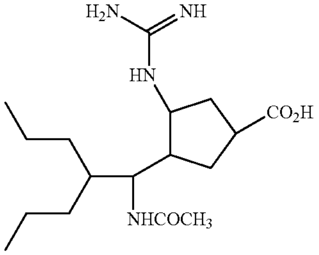

-continued (IV)

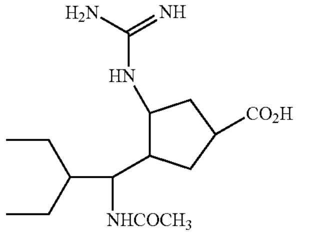

or a pharmaceutically acceptable salt thereof.

9. The method of claim 6, wherein the neuraminidase inhibitor that is administered orally is a compound of formula Ia, IIa, IIIa, or IVa:

(Ia)

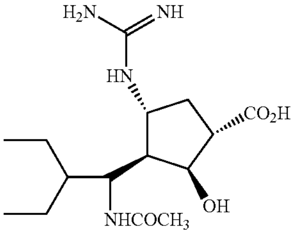

(IIa)

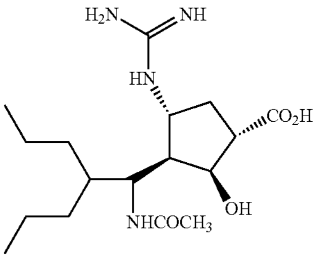

(IIIa)

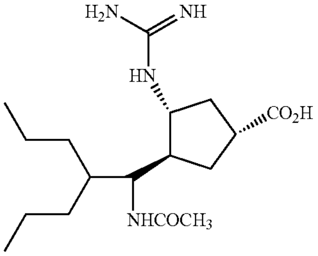

-continued (IVa)

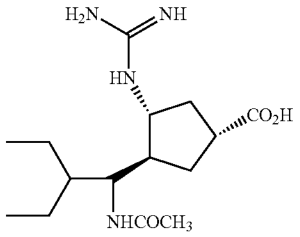

or a pharmaceutically acceptable salt thereof.

10. The method of claim 6, wherein the neuraminidase inhibitor that is administered orally is a compound of formula Ia, Ia

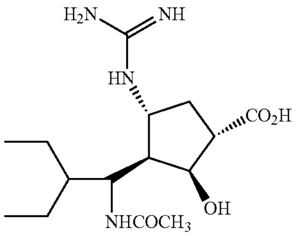

or a pharmaceutically acceptable salt thereof.

11. The method of claim 6, wherein the neuraminidase inhibitor that is administered orally is administered for up to 20 days.

12. The method of claim 6, wherein the neuraminidase inhibitor that is administered orally is administered for up to 10 days.

13. The method of claim 6, wherein the neuraminidase inhibitor that is administered orally is administered for up to 5 days.

* * * * *